US007552492B2

(12) United States Patent
Rolfes et al.

(10) Patent No.: US 7,552,492 B2
(45) Date of Patent: Jun. 30, 2009

(54) HEAD SUPPORT BASE UNIT WITH MULTI-DIRECTIONAL CAPABILITY

(75) Inventors: Sean Rolfes, Cincinnati, OH (US); Charles E. Dinkler, II, Cincinnati, OH (US)

(73) Assignee: Integra LifeSciences Corporation, Plainsboro, NJ (US)

( * ) Notice: Subject to any disclaimer, the term of this patent is extended or adjusted under 35 U.S.C. 154(b) by 89 days.

(21) Appl. No.: 11/525,605

(22) Filed: Sep. 22, 2006

(65) Prior Publication Data

US 2008/0072381 A1 Mar. 27, 2008

(51) Int. Cl.
*A61G 13/12* (2006.01)
(52) U.S. Cl. .................... 5/637; 5/622; 5/643
(58) Field of Classification Search ......... 5/622, 5/637, 640, 643; 297/405–410
See application file for complete search history.

(56) References Cited

U.S. PATENT DOCUMENTS

| | | | |
|---|---|---|---|
| 3,188,079 | A | 6/1965 | Boetcker et al. |
| 4,108,426 | A | 8/1978 | Lindstroem et al. |
| 4,169,478 | A | 10/1979 | Hickmann |
| 4,545,572 | A | 10/1985 | Day |
| 4,964,748 | A | 10/1990 | McFadden |
| 5,317,771 | A | 6/1994 | Cook |
| 5,560,728 | A | 10/1996 | McFadden |
| 5,564,663 | A | 10/1996 | Cook et al. |
| 6,676,669 | B2 | 1/2004 | Charles et al. |
| 7,093,313 | B2 * | 8/2006 | DeBraal et al. ............ 5/622 |
| 7,117,551 | B1 * | 10/2006 | Dinkler et al. ............ 5/637 |

FOREIGN PATENT DOCUMENTS

| | | |
|---|---|---|
| DE | 8802938 U1 | 4/1988 |
| EP | 0992227 | 4/2000 |
| WO | 2004084751 | 10/2004 |
| WO | 2004084751 A2 | 10/2004 |

OTHER PUBLICATIONS

International Search Report, PCT Form Nos. PCT/ISA/220 (Notification of Transmittal), PCT/ISA/210 (International Search Report), and PCT/ISA/237 (Written Opinion).
Pro Med Instruments, *DORO Adjustable Base Unit*, website www.headrest.de, Jun. 27, 2006.

(Continued)

*Primary Examiner*—Fredrick Conley
(74) *Attorney, Agent, or Firm*—Wood, Herron & Evans, L.L.P.

(57) ABSTRACT

A head support base unit enables enhanced capability for positioning the head of a patient at the end of a medical table, by incorporating into the handle assembly thereof an additional degree of freedom, namely rotatability along the longitudinal axis of the handle. More specifically, a pair of axially opposed, spring-biased ratchets are housed within the handle, to permit or prevent axial rotation of one end of the handle relative to the other. This enhanced flexibility an maneuverability is achieved without any added complexity, and without requiring any additional space. These advantages are further magnified if an additional like handle assembly is connected to the first handle assembly, with a link interconnected therebetween, because composite angles and off-axis positioning of the patient can be readily accommodated.

16 Claims, 10 Drawing Sheets

OTHER PUBLICATIONS

Brochure entitled "*Radiolucent Headrest and Retraction System*", Ruggles Instruments, North Quincy, MA.

Brochure entitled "*SUGITA Multi-Purpose Head Frame For Microneurosurgery*", Mizuho.

Codman & Shurtleff, Inc., Brochure, entitled "*Codman Cranial Stabilization System*", Randolph, MA.

Ohio Medical Instruments, Inc., *Heritage of Innovation Cranial Positioning System*, OMI Surgical Products, Cincinnati, OH 1999.

\* cited by examiner

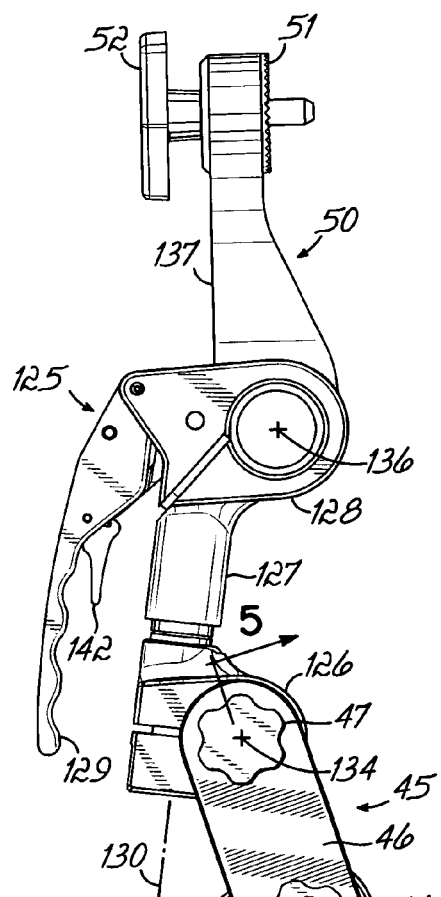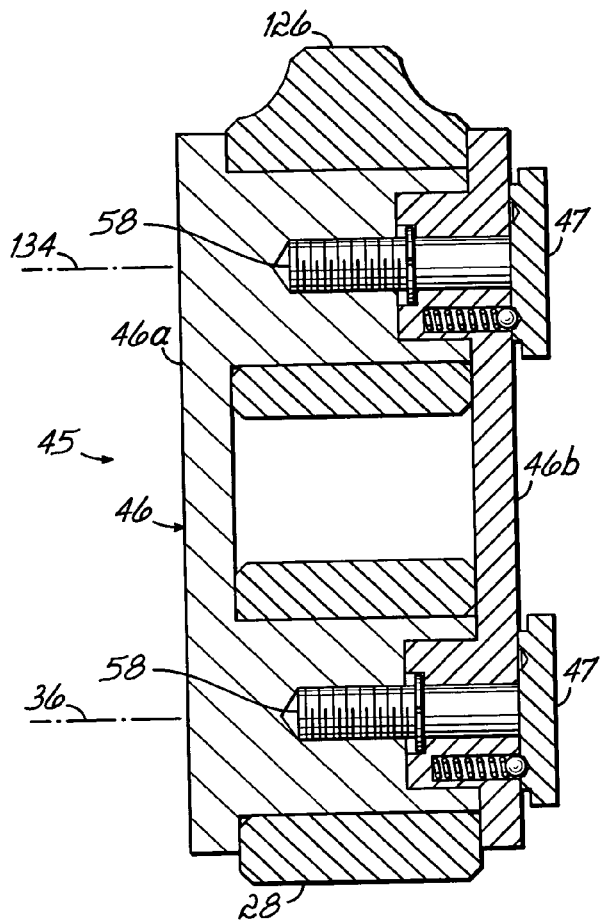
FIG. 5
FIG. 2D

HEAD SUPPORT BASE UNIT WITH MULTI-DIRECTIONAL CAPABILITY

FIELD OF THE INVENTION

This invention relates to a base unit for connecting a head holding device to a medical table, and more particularly, to a base unit which optimizes flexibility, maneuverability, and certainty locating and fixing the head holding device in a desired position relative to the medical table.

BACKGROUND OF THE INVENTION

The assignee of the present application owns U.S. Pat. No. 5,564,663, entitled "Transitional Pivot Joint For Head Support Base Unit," which is expressly incorporated herein by reference, in its entirety (the "'663 patent"). The '663 patent shows a base unit which connects to a medical table. The base unit includes a crossbar and a handle assembly. A transition member connects to the handle assembly, and a swivel adaptor connects to the transition member. Typically, a head holding device, such as a skull clamp or a horseshoe headrest, connects to the swivel adaptor to hold the head of a patient in a desired position relative to the table. Assignee's U.S. Pat. No. 4,169,478, shows a commonly used, well known three-pin skull clamp, and U.S. Pat. No. 5,317,771, shows a well-known horseshoe headrest.

In practical terms, the base unit serves as the intervening hardware that holds the patient's head relative to the medical table. That is, the base unit represents the structural component that connects directly to the medical table, and which in turn supports one or more additional structural components, the last one of which securely holds the head holding device. Usually, the head and upper torso of the patient are cantilevered so as to extend horizontally off the end of the medical table, with the head of the patient fixedly held in place by the head holding device. When the intervening structure of the head holding system includes a base unit, a transition member, and a swivel adaptor, as disclosed in the above-mentioned '663 patent, each of these components is selectively movable relative to each adjacently located component. This enables the neurosurgeon, or the operating room nurse or attendant, to position the patient's head in a desired position relative to the medical table, and then to rigidly clamp these various components together in a desired orientation, to achieve rigid support of the patient's head in the desired position.

More specifically, the base unit has two spaced support rods that connect to the medical table, which in turn support two spaced brackets which hold a horizontal crossbar. A handle assembly of the base unit is oriented transverse to the crossbar, and includes at a first end thereof a first clamp with a first bore that is sized to surround the crossbar. The internal dimension of the first bore is such that the handle assembly may be rotated about the axis of the crossbar, but may also be locked in a fixed position relative to the crossbar when the first clamp is tightened so as to reduce the internal dimension of the bore. The first clamp also enables the handle assembly to be moved horizontally along the crossbar, between the opposing brackets.

The handle assembly of the base unit includes an internal extension bar which extends along an elongated body of the handle assembly, but is fixed adjacent to the first clamp. A lever is pivotally connected to the elongated body, and is also operatively connected to the opposite end of the extension bar. The lever moves relative to the elongated body between: 1) an open unlocked position, in which the bore of the first clamp is enlarged relative to the crossbar and thereby rotatable with respect thereto; and 2) a closed, or locked position in which the internal dimension of the first clamp is reduced to lock the clamp to the crossbar. Thus, movement of the lever between the open and the closed positions enables the handle assembly to be rotatable or fixed, respectively, relative to the crossbar via the first clamp.

The handle assembly also includes a second clamp at a second end thereof, which defines a second bore spaced from and oriented parallel to the first bore. As with the first bore, the second bore has an internal dimension which varies, depending upon the position of the lever relative to the elongated body. The second bore of the handle assembly is sized to removably hold a shaft mounted transversely at one end of the transition member.

Thus, when the lever is in the open position relative to the handle assembly, the handle assembly is rotatable about the first axis, i.e. around the crossbar, and the transition member is also rotatable about a second spaced axis which is parallel with the first. Once rotated to the desired position, these components can be locked in place by closing the lever. The opposite end of the transition member typically includes a combination threaded/star burst connection to enable a first end of a conventional swivel adaptor to connect to the transition member. An opposite end of the swivel adaptor includes another combination threaded/star burst connection, for rigid securement thereto of the desired head holding device. These threaded star burst connections at the opposite ends of the swivel adaptor provide additional maneuverability for this head holding support system.

This combination of selectively movable components, including the intervening clamps and connectors, provides stable and secure fixation of a patient relative to the medical table, with a high degree of reliability and consistency, as is needed for brain surgery. In fact, the head holding devices shown in these U.S. patents are recognized by neurosurgeons around the world as representing the gold standard in terms of achieving a high degree of head fixation and stability with respect to holding the head of a patient during brain surgery. Although others have tried to mimic these head holding devices and these systems, for one reason or another they have not been as successful as assignee, or its predecessor, in consistently achieving the desired degree of patient fixation relative to a medical table.

Despite its long track record of success for these head holding products, assignee seeks to continue to improve upon the performance of such cranial stabilization devices, in an effort to continue to meet the needs of neurosurgeons around the world. But with respect to enhanced maneuverability, this goal is more easily wished for than actually achieved. That is because each additional component requires additional structure for permitting selective movement relative to the adjacently located components, and also the necessary structure for locking the component in the selected position. So adding an additional degree of maneuverability generally requires another connector, and also occupies additional space. Also, in the operating room it can also be important for the operation of these components to be readily understood and user-friendly, so a completely different structure could lack the degree of familiarity of the well-known components currently used.

Also, in some instances, the time and convenience of maneuvering these head holding components into the correct position can be critical. Because of the multiple connection points of the various intervening components, it is possible that inexperienced operating room personnel may initially connect the components in an incorrect manner, such that the components need to be disconnected and then properly connected in order to securely hold the patient in the desired position. Also, some of these intermediate pieces come in different sizes. For instance, the transition member typically comes in two standard lengths, three inches and six inches. Such size variations can create questions among operating room personnel as to the most preferred, or most appropriate, components to use for holding a patient in a particular situation.

It is one object of the invention to enhance the flexibility and versatility of a head holding structure used to maneuver and support a patient in a desired position at the end of a medical table.

It is another object of the invention to simplify the decisions, the procedures, and/or the components needed by neurosurgeons or operating room attendants for correctly locating a patient's head in a desired position relative to the end of the medical table, and then firmly securing the patient's head in that desired position.

It is still another object of the invention to accomplish these objectives with structure that is reasonably familiar to neurosurgeons and operating room personnel, and which does not occupy an excessive amount of three dimensional space.

SUMMARY OF THE INVENTION

The present invention achieves the above-stated objects by incorporating an internal clutch mechanism into the elongated body of the handle assembly, to enable an outboard second section of the handle assembly to rotate axially relative to an inboard first section.

With rotatability along the longitudinal axis, the axis of a second clamp, located opposite the crossbar and a first clamp, may be selectively rotated to an orientation that is non-parallel with the connecting tube, and then locked in place at that selected orientation. In addition to this axial rotatability, this handle assembly still permits the conventional translational movement along the crossbar, rotational movement about the crossbar, and rotational movement at the second clamp. But with this additional degree of freedom, and hence this additional maneuverability, this base unit greatly enhances flexibility and maneuverability in locating and fixing a patient in a desired position relative to a medical table, without adding any additional knobs or securement devices, and without taking up more space.

To do this, this inventive base unit uses a lever which operatively connects to one end of an extension bar with the extension bar extending along and inside the body of a handle assembly. The extension bar is fixed at one end of the body, adjacent the crossbar. Movement of the lever relative to the body causes the extension bar to simultaneously open or close a pair of spaced clamps that are located at opposite ends of the body. But at the same time, the movement of the lever and the extension bar also causes a pair of internal spring-biased, axially opposed ratchets to either engage or disengage along the longitudinal axis of the body. When the ratchets are disengaged, one end of the body is axially rotatable relative to the opposite end. When the ratchets are engaged, the two ends of the body are axially fixed relative to each other. Thus, these spring-biased axially opposed ratchets serve as an internal clutch mechanism. Preferably, the lever and this internal clutch mechanism generally occupy the same volume as existing base units.

Because this handle assembly is preferably sized and shaped similar to existing base units, this invention provides these advantages in a manner that is readily understood by neurosurgeons and operating room personnel. Stated another way, this invention supplies these advantages in a user-friendly way, by modifying existing conventional components.

For all of these reasons, the base unit of the present invention can be substituted for the prior conventional base unit to achieve numerous and immediate advantages. Also, at least one additional like handle assembly can be operatively connected to the first handle assembly, preferably with a link interconnected therebetween. This additional like handle assembly provides additional maneuverability for the interconnected head holding system, because it provides rotatability along the additional longitudinal axis of the additional handle assembly, in addition to providing the conventional degrees of freedom via the spaced clamps located at opposite ends thereof. This structure significantly enhances the flexibility of positioning a head support device that is operatively secured to the outer end of the additional handle assembly. In fact, the use of two or more such handle assemblies causes the interconnected components to have an almost snake-like ability to accommodate any desired patient position.

With this added flexibility and maneuverability, the need for stocking differently sized transitional members is eliminated. One modified size will suffice to accommodate any desired patient position. Also, the need for the conventional swivel adaptor is eliminated completely, along with its two knobs which typically require manual tightening and loosening. In contrast, the modified transition member includes only one knob. Instead, for each of the handle assemblies the lever opens to provide the benefit of additional degrees of freedom relative to the crossbar, and then closes to lock in the selected position for the patient.

According to one aspect of the invention, handle assembly includes structure for affirmatively holding the lever in the closed position. According to the preferred embodiment of the invention, with axial rotatability about the handle body, this can be achieved via a trigger-like latch pivotally mounted to the lever. Another structural option for supplying this feature would be a wire catch. In fact, the present invention contemplates the possibility of applying this inventive principle, namely an affirmative lock mechanism, to existing conventional base units. That could be done in a number of different ways, but perhaps most conveniently with a wire catch mounted to the end of the lever, and adapted to engage the existing body of the conventional handle assembly.

These and other features of the invention will be more readily understood in view of the following detailed description, and the drawings.

BRIEF DESCRIPTION OF THE DRAWINGS

FIG. 2B shows a medical table and also a skull clamp held by the additional handle assembly, via the intervening modified transition member.

FIG. 2D is a side view of the same variation of the invention as shown in FIGS. 2A and 2C.

FIG. 5 is a longitudinal cross sectional view taken along line 5-5 of FIG. 2D, showing the link which interconnects the first and second handle assemblies, in accordance with the embodiment of the invention shown in FIGS. 2A, 2B, 2C and 2D.

DETAILED DESCRIPTION OF THE PREFERRED EMBODIMENTS

Figure 1:
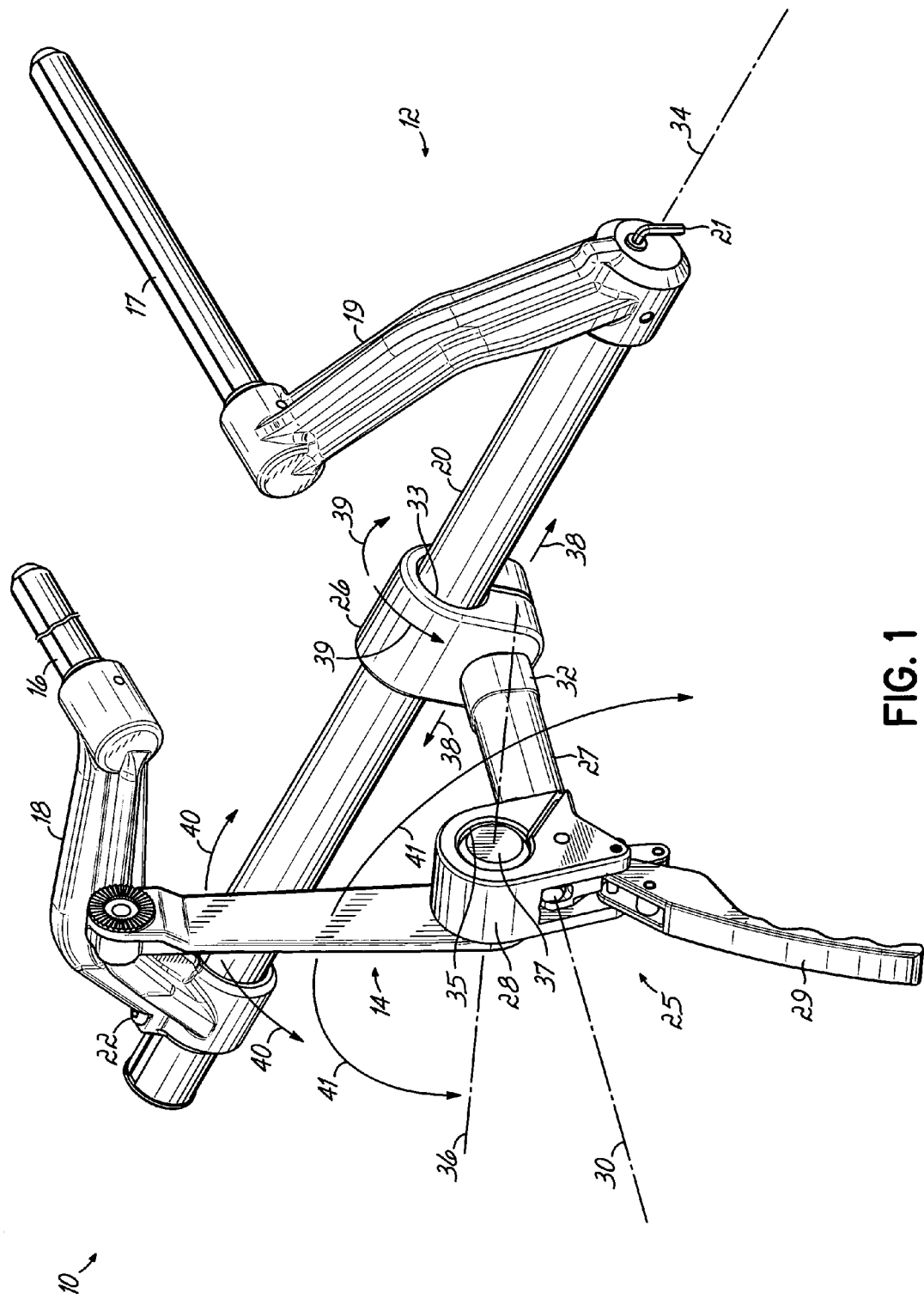
FIG. 1 is perspective view which shows a first preferred embodiment of the invention, with a first handle assembly supporting a transitional member in a desired position relative to a connecting tube, and the lever of first handle assembly in an open, unlocked position.

FIG. 1 shows a head support system 10 constructed in accordance with a first preferred embodiment of the invention, for holding the head of a patient (not shown) in a desired position relative to a medical table (not shown). The system 10 includes a base unit 12 and a conventional transition member 14. FIG. 1 shows that the primary advantages of the present invention can be achieved with relatively few components, and also by using some of the existing conventional cranial stabilization components, such as a conventional transition member 14.

The base unit 12 of the present invention includes a pair of spaced support rods, 16 and 17. A corresponding set of brackets 18 and 19, respectively, hold the support rods 16 and 17 in parallel. A crossbar 20, also sometimes referred to as a connecting tube, spans the horizontal distance between the brackets 18 and 19, and the brackets 18 and 19 hold the connecting tube 20 in a fixed position so that there is no relative rotation therebetween. In this application, the words connecting tube and crossbar are used interchangeably, and the word tube does not necessarily mean that the structure is hollow. At one end of the connecting tube 20, and in this case the end where bracket 19 connects thereto, a hex key wrench 21 is threadably held by the bracket 19 and removable therefrom to allow the adjusting of bracket 18 via button head screw 22. This screw 22 is located on the bracket 18 at the other end of the connecting tube 20, and it may be loosened to permit translational movement of bracket 18 along the connecting tube 20, thereby to vary the spacing between support rods 16 and 17 to accommodate some variation in the differently spaced mounting structures used by medical tables.

In accordance with the invention, the base unit 12 includes a handle assembly 25 which has a first clamp 26 located at a first end thereof, which circumscribes the connecting tube 20. The handle assembly also includes an elongated body 27 and a second clamp 28 located at a second end thereof. A lever 29 hingedly connects to the elongated body 27. The lever 29 pivotally moves between an open, unlocked position, as shown in FIG. 1, and a closed, locked position.

At the first end of the elongated body 27, the first clamp 26 includes an internal bore 33 which is aligned along a first axis 34. The first axis 34 is also the axis of the connecting tube 20. The second end of the handle assembly 25 includes a second bore 35 which defines a second axis 36. FIG. 1 shows a transversely oriented shaft 37 located at one end of the transition member 14, which extends into the bore 35 and along second axis 36. Adjacent the first clamp 26 at the first end, the handle assembly 25 includes a reinforcing sleeve 32.

As with conventional base units, the base unit 12 of the present invention is movable laterally along the connecting tube 20, as shown by directional arrows 38, when the lever 29 is unlocked. Moreover, directional arrows 39 show the rotational capability of the handle assembly 25 relative to first axis 34, when the lever 29 is unlocked. Directional arrows 40 show the rotational capability about the second axis 36. In contrast, when the lever 29 is moved to a locked position, preferably adjacent to the body 27, the movements depicted by directional arrows 38 and 39 are prevented. Also, the closing of lever 29 relative to elongated body 27 causes the second clamp 28 to securely engage the shaft 37 of the transition member 14, thereby to rigidly hold the transition member 14 in a desired position relative to the handle assembly 25. These three capabilities, namely lateral movement along the connecting tube 20, rotational movement about the connecting tube 20 (also the first axis 34), and rotational movement about the second axis 36, are conventional with base units that are commercially available. And the degrees of freedom and maneuverability provided by such conventional base units has enabled neurosurgeons to rigidly hold a patient's head in a desired position relative to a medical table.

But the base unit 12 of the present invention improves upon these prior capabilities by also enabling axial rotatability of the second clamp 28 about a handle axis 30 which extends along the elongated body 27. This additional degree of freedom, i.e., rotatability about axis 30, as shown by directional arrows 41, enhances the ability of a neurosurgeon or an operating room attendant to securely hold a patient in a desired position relative to a medical table, wherein the position may be angled or offset relative to the longitudinal axis of the table. More specifically, when lever 29 is in an open or unlocked position relative to elongated body 27, the second axis 36 may be reoriented at an angle which is no longer parallel with first axis 34. Previously, with conventional base units these spaced axes always remained in parallel orientation.

Figure 2A:
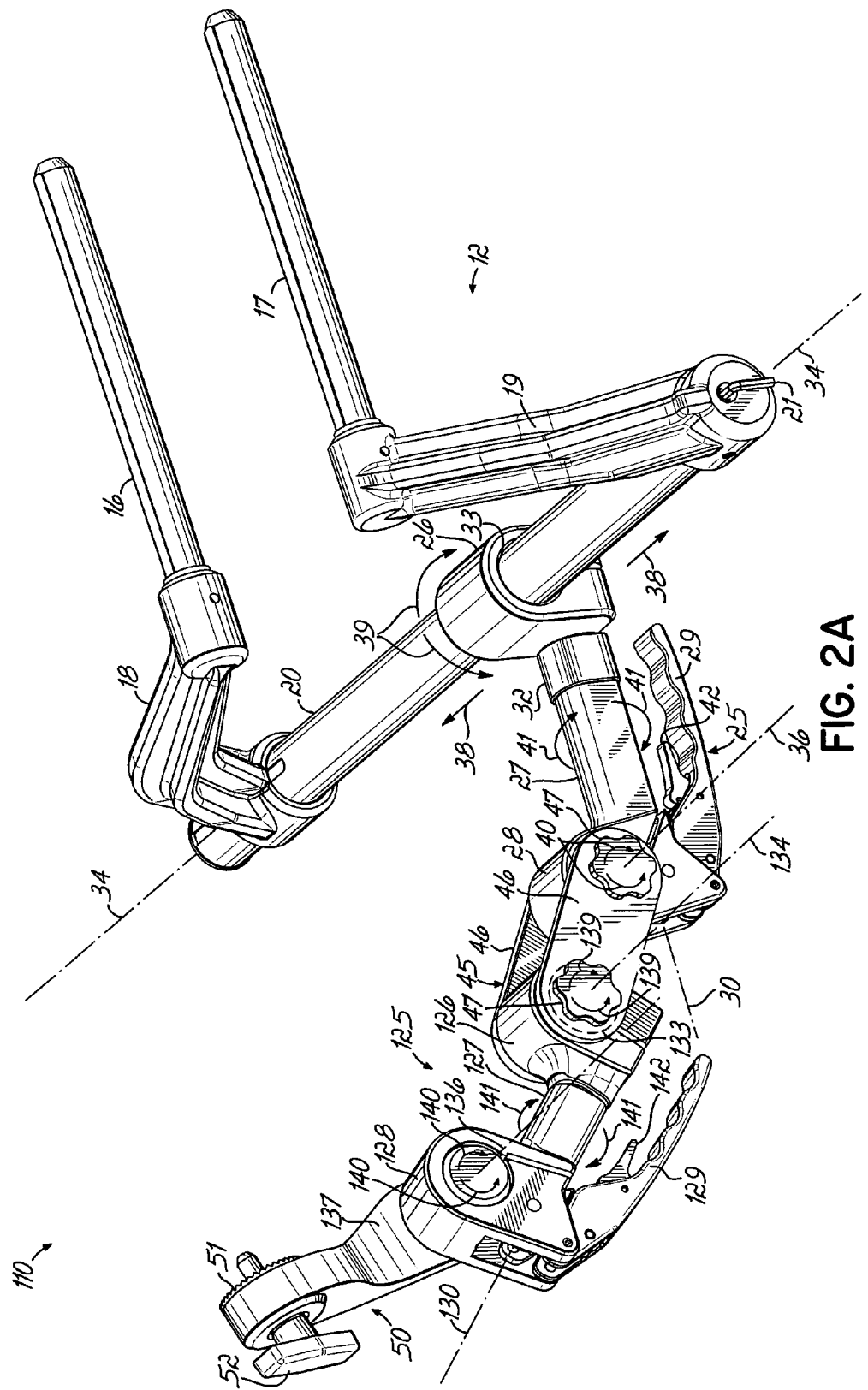
FIG. 2A is a perspective view which shows a variation of the first preferred embodiment of the invention that is shown in FIG. 1, with an additional handle assembly connected to the first handle assembly via an intervening link, and a modified transition member connected to the additional handle assembly.

FIG. 2A shows a head support system 110 which is slightly varied from the head support system 10 shown in FIG. 1. More specifically, FIG. 2A again shows the same spaced rods 16, 17, brackets 18, 19, connecting tube 20, and first handle assembly 25, including the first clamp 26 and the second clamp 28. FIG. 2A shows lever 29 in a closed, or locked position, to inhibit rotation about axis 30. Rotational arrows 39, 40, and 41 depict the rotational degrees of freedom, i.e. the maneuverability, permitted by the present invention, including rotation about the longitudinal axis 30 of the elongated body 27. Notably, it is not only the second clamp 28 of first handle assembly 25 which is rotatable about longitudinal axis 30 with respect to the first clamp 26 when lever 29 is in an unlocked position, but also all of the additional components that are connected to second clamp 28.

FIG. 2A shows a latch 42 which pivotally connects to the lever 29. The latch 42 holds or retains the lever 29 in the closed, locked position, relative to elongated body 27. By pivoting the outer end of latch 42 in a trigger-like movement, the lever 29 may be moved to the unlocked position. This latching mechanism 42 provides an added degree of assurance to the neurosurgeon that the lever 29 will remain in the closed, locked position until someone in the operating room makes an affirmative decision to unlock the lever 29. With the base unit 12 of this invention, particularly with the latch 42 as shown and described herein, the first handle assembly 25 could be constructed so that a reduced, or more moderate, amount of opening force is needed to move the lever 29 from the closed position. That could make the first handle assembly 25 more convenient in use.

FIG. 2A also shows an additional handle assembly 125 operatively connected to the first handle assembly 25, via an interconnected link 45. More specifically, the link 45 includes a pair of parallel, spaced members 46 which are held together by spaced connectors, which include a pair of adjustable knobs 47. In FIG. 2A, an innermost end of the link 45 connects to first handle assembly 25 at the second clamp 28. An opposite or outermost end of the link 45 connects to an additional first clamp 126 located at the first end of the additional handle assembly 125. Just as first clamp 26 is aligned along the first axis 34, the additional first clamp 126 includes an additional bore 133 aligned along an additional first axis 134.

As with the first handle assembly 25, the additional handle assembly 125 also includes an additional second clamp 128, located at a second end thereof, and an additional elongated body 127 which extends along the additional handle assembly 125 and defines an additional longitudinal axis 130.

The additional handle assembly 125 includes an additional lever 129 and an additional latch, 142, which essentially operate in the same manner as the lever 29 and the latch 42 previously described with respect to FIG. 1. That is, when the lever 129 moves to a closed position, which in FIG. 2A is shown adjacent the additional elongated body 127, the additional second clamp 128 and the additional first clamp 126 are closed to their smaller dimension, tightened configuration, to prevent rotational movement about additional first axis 134 and additional second axis 136. In this closed position, the additional second clamp 128 is also prevented from axially rotating about additional longitudinal axis 130.

Conversely, when the additional lever 129 is moved to an open position, the additional handle assembly 125 is axially rotatable about additional axis 130, relative to additional first clamp 126, as shown by reference arrows 141. And there is also rotational capability about spaced first and second additional axes 134 and 136, as shown by directional arrows 139 and 140.

In this way, the first handle assembly 25 and the additional handle assembly 125 are stacked, or cascaded in series, via the intervening link 45. Importantly, the link 45 is in one sense a passive interconnection element, because it can remain secured to the second clamp 28 and the additional first clamp 126, if desired. In other words, the spaced knobs 47 do not have to be manipulated every time this head support system 110 is used. When the link 45 remains fixed, the two like handle assemblies 25 and 125 provide seven degrees of freedom when both levers 29 and 129 are open. And by the simple closing motion of these levers 29, 129, these seven degrees of freedom are prevented.

At the outermost end of this head support structure 110, the additional second clamp 128 holds a modified transition member 50. This modified transition member 50 includes a body 137 and a transverse hub 140 which extends along the additional second axis 136 of the additional second clamp 128. This modified transition member 50 includes a connecting surface which includes a starburst ratchet connection 51 and a threaded connector which is controllable via a knob 52, in cooperation with the starburst connection 51. Preferably, the knob 52 is operable to securely hold a head holding device in position relative to the modified transition member 50. In that way, only levers 29 and 129 need to be opened in order to manipulate the head support system 110 into a desired position, and then closed in order to fix the modified transition member 50, and the head holding device attached thereto, in that desired position.

Figure 2B:
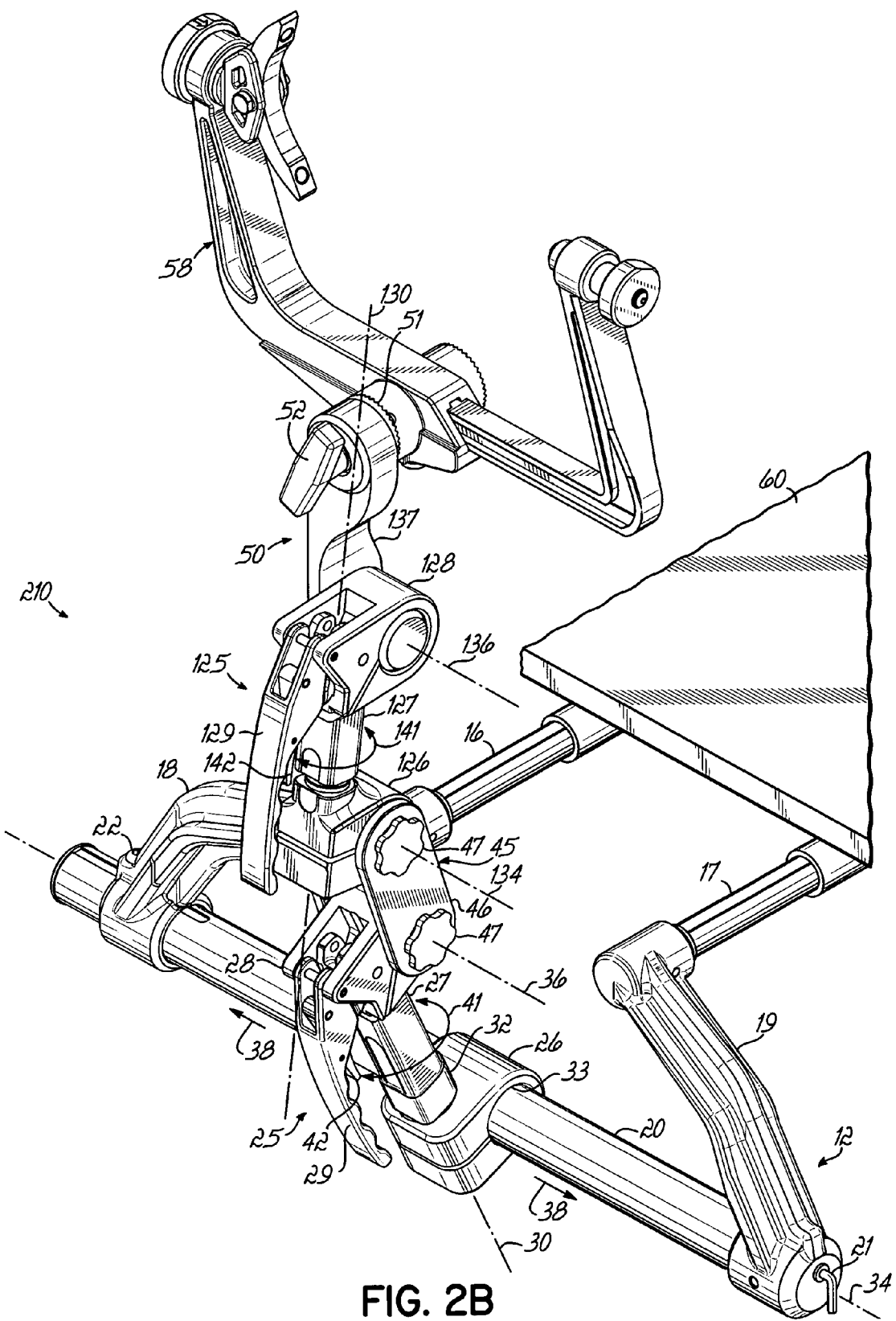
FIG. 2B is a perspective view which shows another variation of the invention shown in FIGS. 1 and 2A. More specifically.

FIG. 2B shows a conventional three pin skull clamp 58 connected to the modified transition member 50, in essentially the same way that conventional skull clamps connect to conventional swivel adaptors. FIG. 2B also shows the rods 16 and 17 connected to a medical table 60. With the head support system 210 as shown in FIG. 2B, multiple degrees of freedom are achieved by opening the levers 29 and 129 of the first handle assembly 25 and the additional handle assembly 125. For instance, with both levers 29 and 129 in the open position, all the structural components which are outboard of the first clamp 26 are translatable along the connecting tube 20, rotatable with respect to the connecting tube 20, and rotatable about axis 30, as represented by directional arrows 41. Additionally, all of the components outboard of second clamp 28 are rotatable with respect to second axis 36. Everything outboard of additional first clamp 126 is rotatable with respect to additional first axis 134, and also axially rotatable about axis 130, as shown by directional arrows 141. All components outboard of the additional second clamp 128 are also rotatable with respect to the additional second axis 136.

This head support system 210 has multi-directional capability for positioning the skull clamp 58 in a desired position relative to the medical table 60 by providing seven degrees of freedom relative to the medical table 60. This head support system 210 can be maneuvered into virtually any desired position. And particularly because of the axial rotatability about axes 30 and 130, as shown via reference numerals 41 and 141, this head support system 210 achieves an almost snake-like movement to the desired position.

Figure 2C:
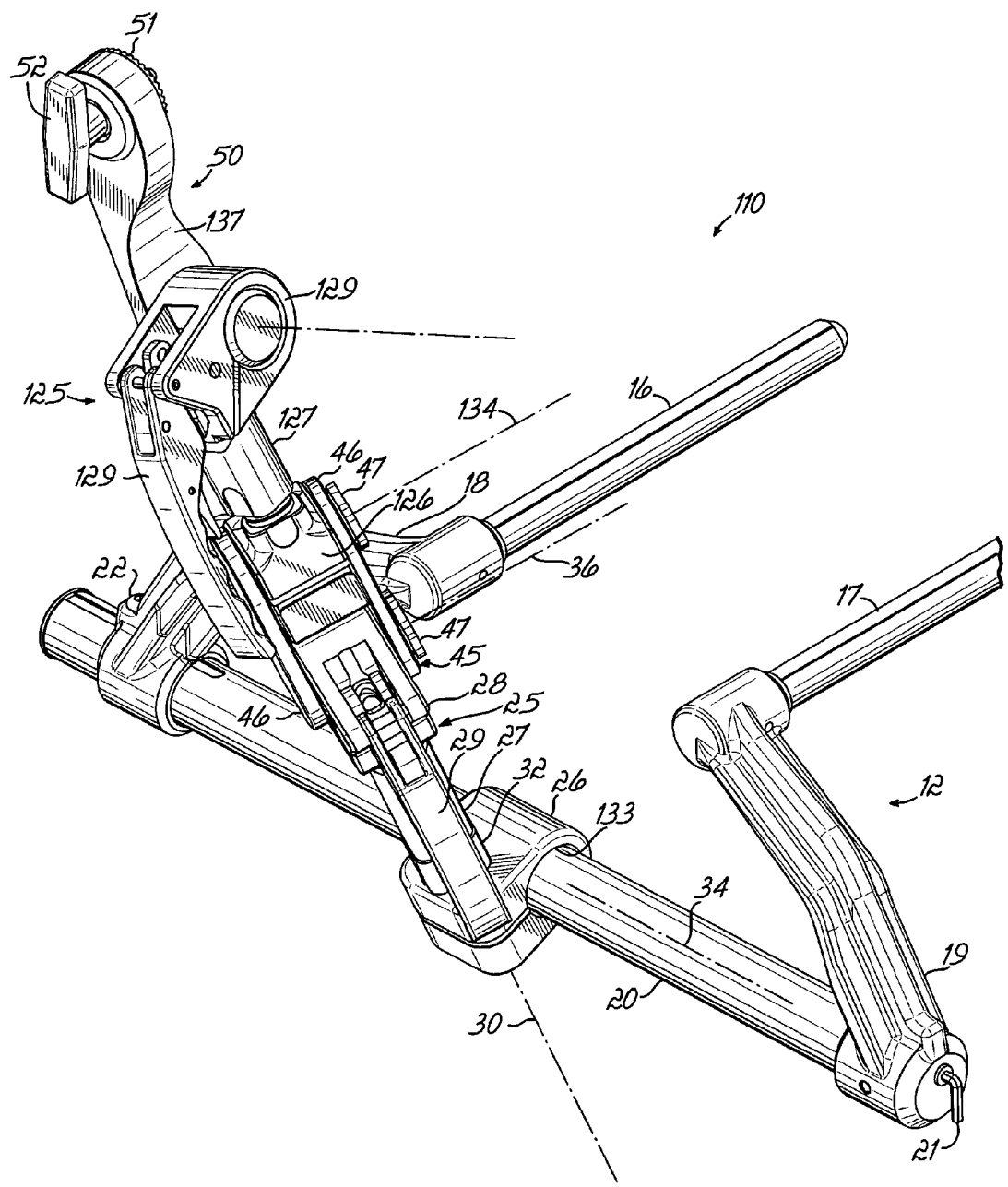
FIG. 2C shows the same construction of the invention as shown in FIG. 2A, but with the first handle assembly, the additional handle assembly, the intervening link, and the modified transition member arranged in a different orientation.

FIG. 2C shows the same structural components as previously shown in FIG. 2A. Thus, FIG. 2C uses the same reference numerals for those some components. Nonetheless, FIG. 2C shows the capability for axially rotating the body 27 of the first clamp assembly 25 with respect to its longitudinal axis 30, to reorient the second axis 36 of the second clamp 28 to an orientation that is no longer parallel with the first axis 34 of the first clamp 26. Thus, FIG. 2C also shows that the lever 29 and the additional lever 129 do not need to be aligned when in use.

FIG. 2D shows a side view of the same structure shown in FIGS. 2A and 2C. Therefore, identical reference numerals are again used in FIG. 2D.

Figure 2E:
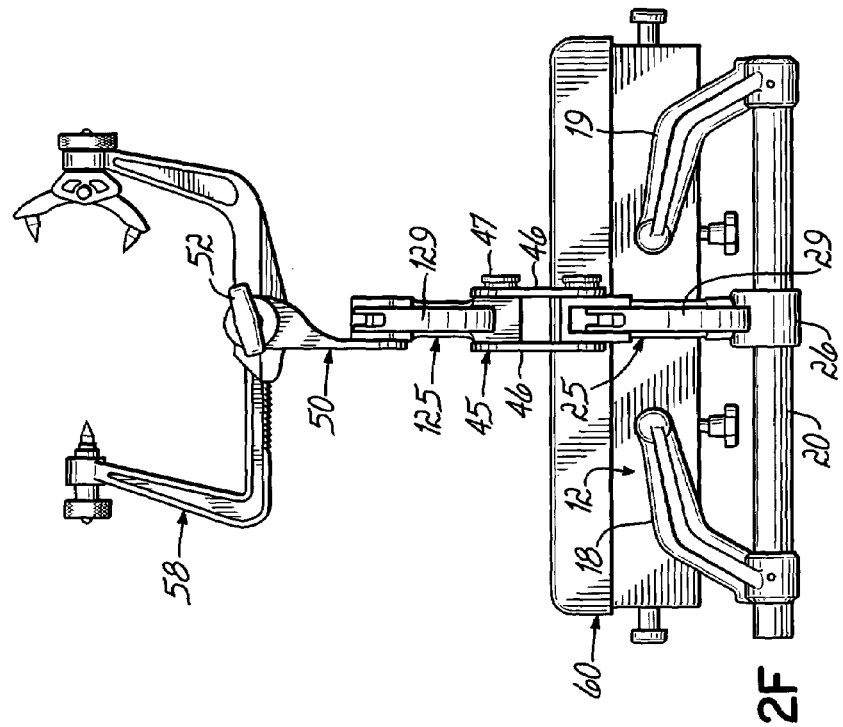
FIGS. 2E and 2F are longitudinal views showing two orientations of the present invention, connected to a table, with the brackets directed upwardly, as shown in FIG. 2E, or downwardly, as shown in FIG. 2F.
Figure 2F:
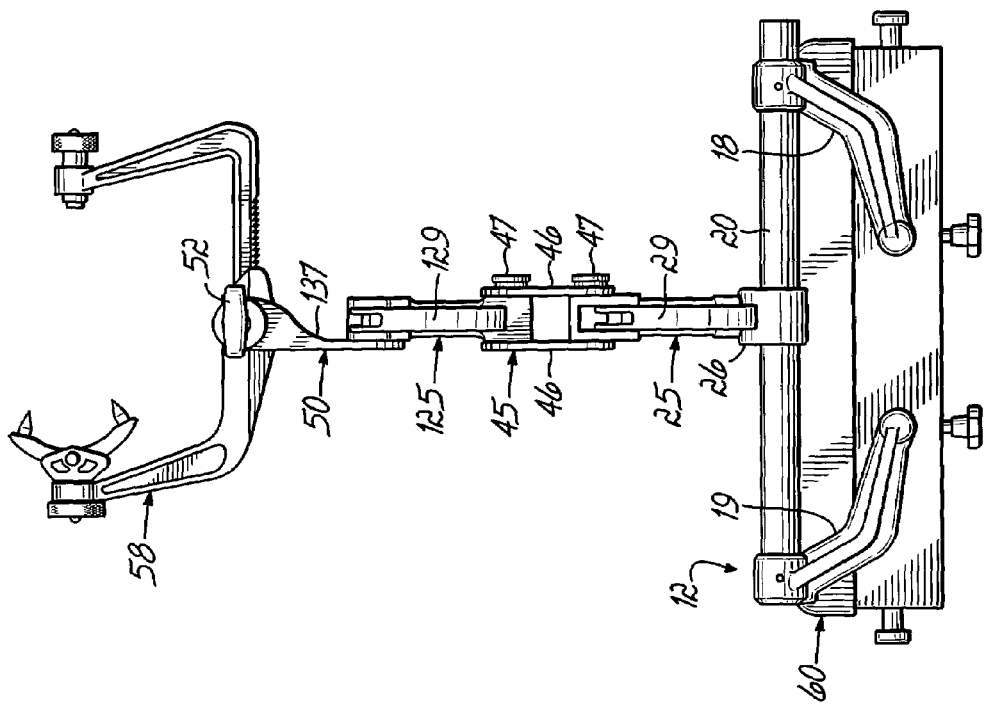

FIGS. 2E and 2F illustrate the ability to connect the rods 16 and 17 to the table so that the brackets 18 and 19 extend either upwardly, as shown on the left, or downwardly, as shown on the right. The body 27 rotates with respect to the cross bar 20 to accommodate this. These two different configurations produce a difference in vertical height of about 8 inches.

With prior base units, it was theoretically possible to connect the brackets so as to extend either downwardly or upwardly. However, the lever position was axially fixed relative to the body. Thus, such an inversion of the brackets would place the lever on the inside of the body, between the table and the body of the base unit. In that location, the lever would be difficult to open and close. In contrast, with the present invention, regardless of whether the brackets 18 and 19 extend upwardly or downwardly, the body 27 can be axially rotated to place the lever 29 outboard, or outside of, the body 27.

Figure 3A:
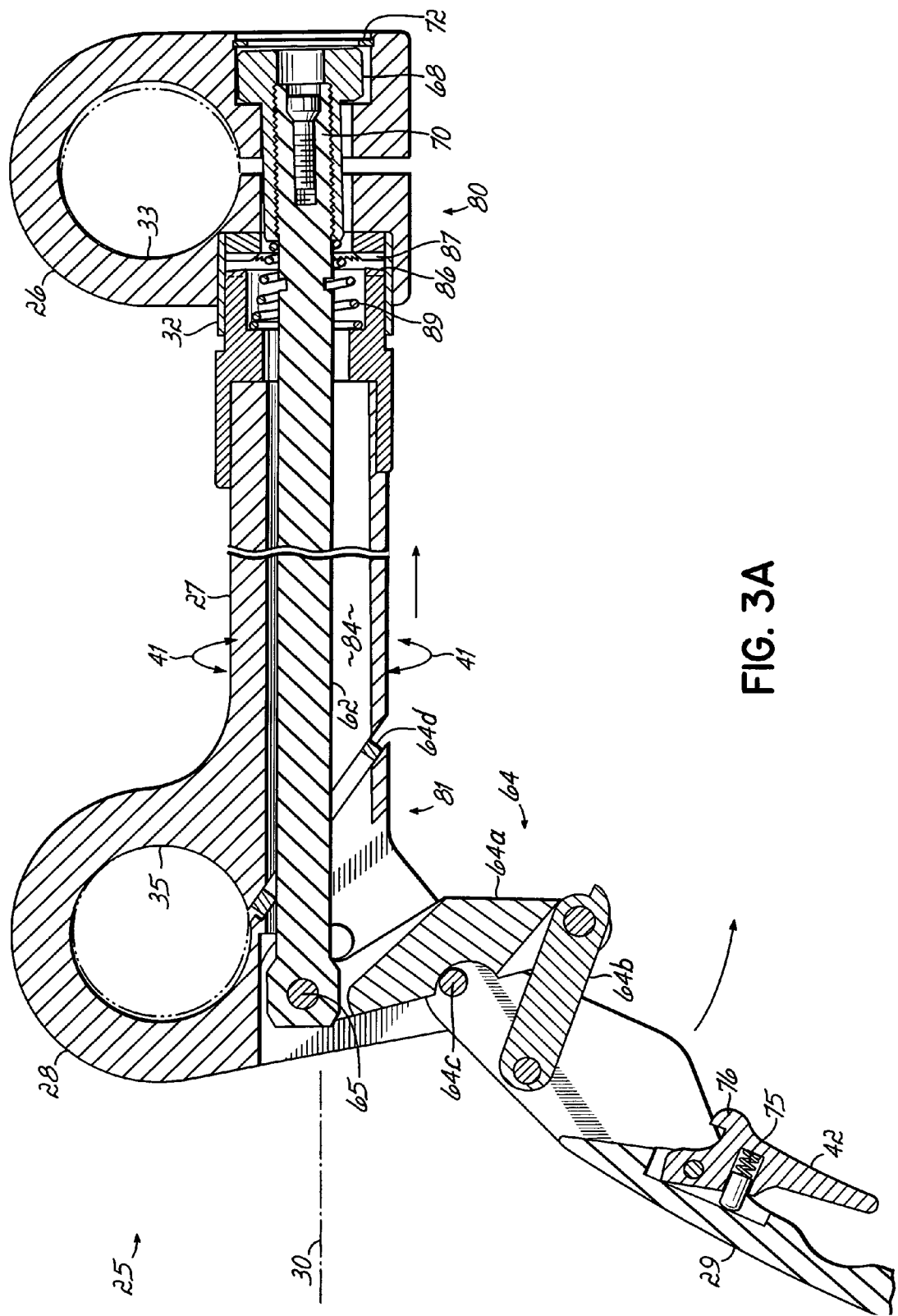
FIG. 3A is a longitudinal cross sectional view of the first handle assembly in accordance with a first preferred embodiment of the invention, with the lever in an open, unlocked position.
Figure 3B:
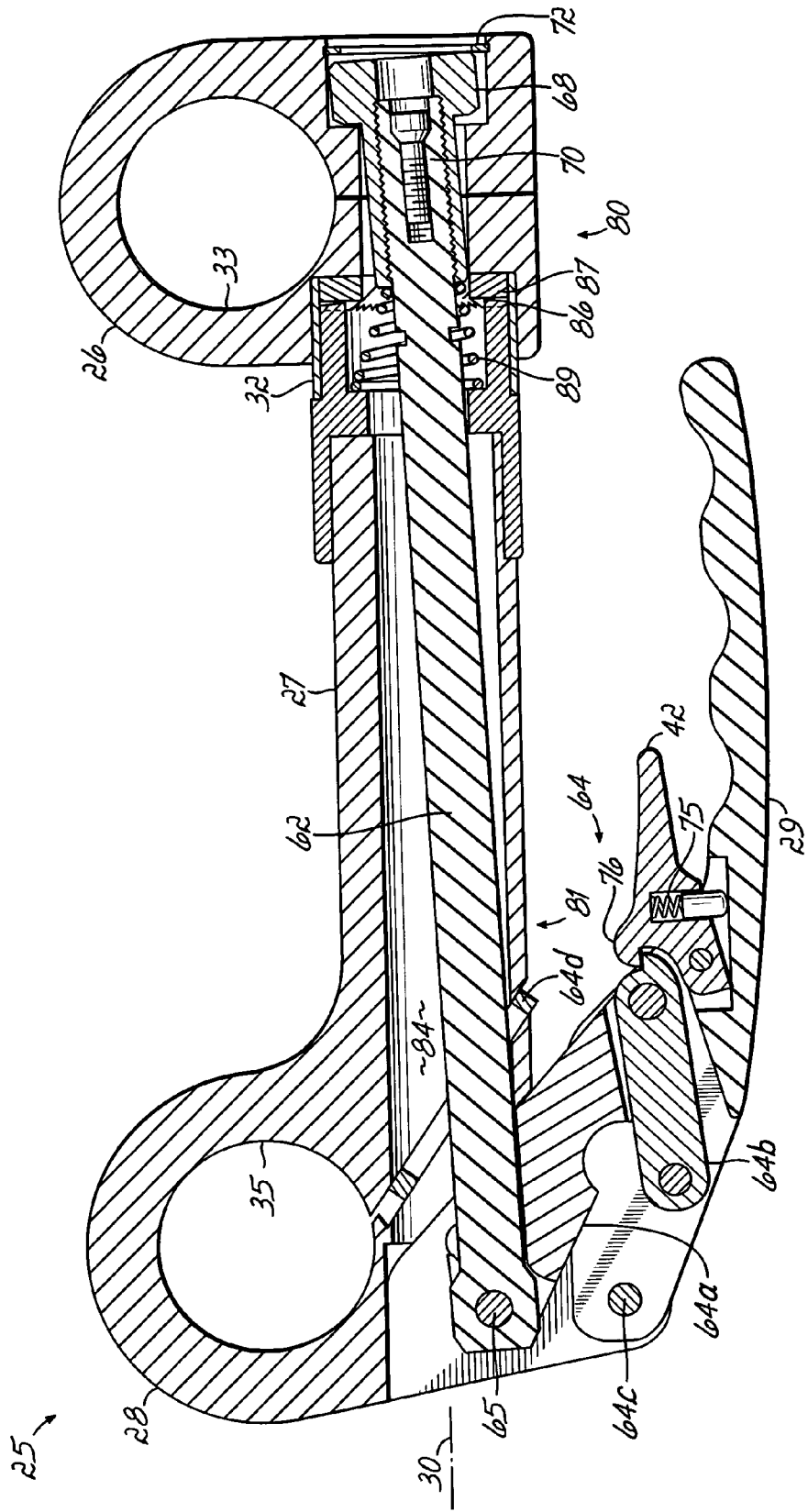
FIG. 3B is a longitudinal cross sectional view of the first handle assembly, similar to FIG. 3A, but with the lever in a closed, locked position.

FIG. 3A shows the first handle assembly 25 with the lever 29 in an open position, and FIG. 3B shows the same view with the lever 29 in a closed position. In FIG. 3A, the phantom lines within the first clamp 26 and within second clamp 28 show the reduced internal dimensions of the clamps when lever 29 is closed, as is known. FIG. 3A also shows an extension bar 62 which operatively connects to the lever 29, via a linkage 64 and a pin 65, at the second end of the body 27. At the first end of the body 27, the extension bar 62 has external threads which cooperate with internal threads of a T-shaped collar 68, which also has an axial bore therethrough. This structure fixes a first end 70 of the extension bar 62 to the first end of the body 27, preferably with a ring 72 mounted at the outer end.

FIG. 3B shows the extension bar 62 slightly angled relative to the first end of the handle assembly 25, when the lever 29 is closed. A set screw threadably holds the extension bar 62 at the first end of the handle assembly 25, adjacent first clamp 26.

In practical terms, FIGS. 3A and 3B show that the elongated body 27 of first handle assembly 25 essentially includes a first section 80 located adjacent the first clamp 26, and a second section 81 located adjacent the second clamp 28. The extension bar 62 resides within a hollow space 84 defined by the first 80 and second 81 sections. Within this hollow space 84, the first and second sections 80, 81 carry an internal clutch mechanism, preferably two axially aligned ratchets 86, 87. These ratchets 86, 87 are biased away from each other, via an axial spring 89, when the lever 29 is in the open position. When the lever 29 is closed, the axial pulling force applied by extension bar 62 overcomes the bias of the spring 89, to move the ratchets 86, 87 axially closer together to cause the axially opposed ratchet teeth thereof to intermesh, to thereby prevent relative rotation of the second section 81 and the first section 80 with respect to axis 30. Thus, it is this internally located clutch mechanism, preferably a pair of axially spaced, spring-biased ratchets 86, 87, which permits or prohibits rotation of the second section 81 relative to the first section 80 about axis 30.

FIGS. 3A and 3B also show a sleeve 32 located adjacent first clamp 26. This sleeve provides additional structural integrity to the first handle assembly 25, adjacent to the first clamp 26. Aside from this sleeve 32 and a slightly shorter longitudinal dimension, the additional handle assembly 125 is in all material respects the same as the first handle assembly 25. In other words, the additional handle assembly 125 is like first handle assembly 25 in terms of functionality, i.e. axial rotatability, and the structure which supplies this functionality, although the relative shapes of these components may vary, as desired.

Figure 4:
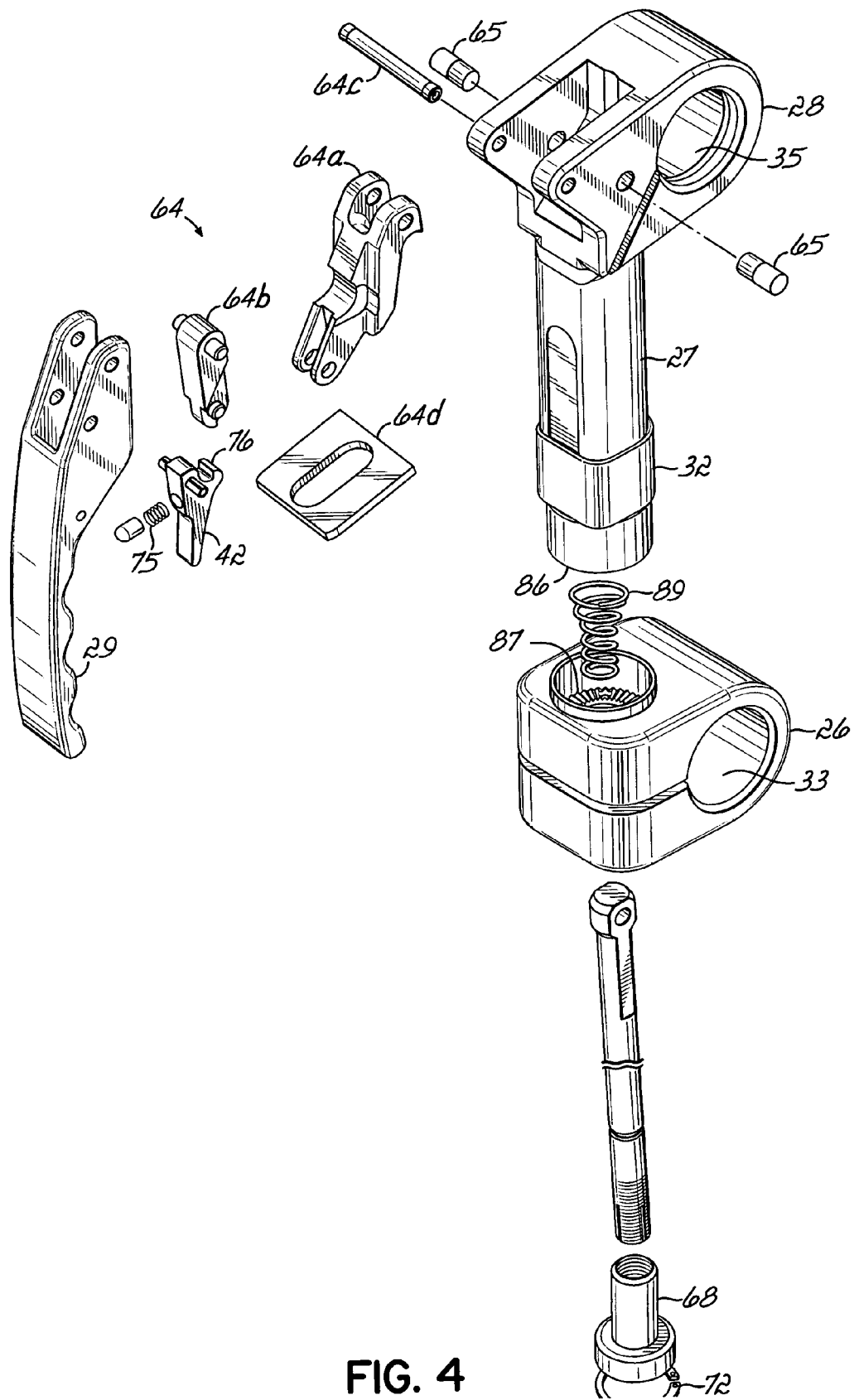
FIG. 4 is a disassembled perspective view of the first handle assembly, in accordance with the first preferred embodiment of the invention.

FIG. 4 shows an exploded view of the components of the first handle assembly 25. FIG. 4, in connection with FIGS. 3A and 3B, also shows the structural details of the latch 42 which is held by a spring 75, to enable it to be moved in trigger-like fashion toward lever 29 in order to release lever 29 from the locked position. This trigger-like mechanism includes a catch 76 which engages a complementarily shaped surface formed on one component 64b of the linkage 64, the components of the linkage 64 are designated via reference numerals 64a, 64b, 64c, and 64d, and they generally correspond to structure used in conventional base units, as is known in this field.

FIG. 5 shows a transverse cross sectional view along cross sectional line 5-5 of FIG. 2D. More particularly, FIG. 5 shows the internal structure of the link 45, which interconnects the first handle assembly 25 with the additional handle assembly 125. More specifically, FIG. 5 shows a portion of the second clamp 28, and a portion of the additional first clamp 126, surrounding spaced hub-like portions of member 46a. A complementarily-shaped member 46b includes protruding sections which extend into recesses formed within the hubs of member 46a. The two opposing members 46a and 46b are held in place on the second clamp 28 and the first additional clamp 126 by tightening the knobs 47, to achieve securement via the threads at the internal ends 58 thereof. This interconnects the link 45 to the first handle assembly 25 and the additional handle assembly 125, while still permitting rotation about axis 36 and also axis 134.

FIG. 5 shows that the knobs 47 can be unscrewed to disconnect the members 46a and 46b, thereby to disconnect the first handle assembly 25 and the additional handle assembly 125.

Figure 6:
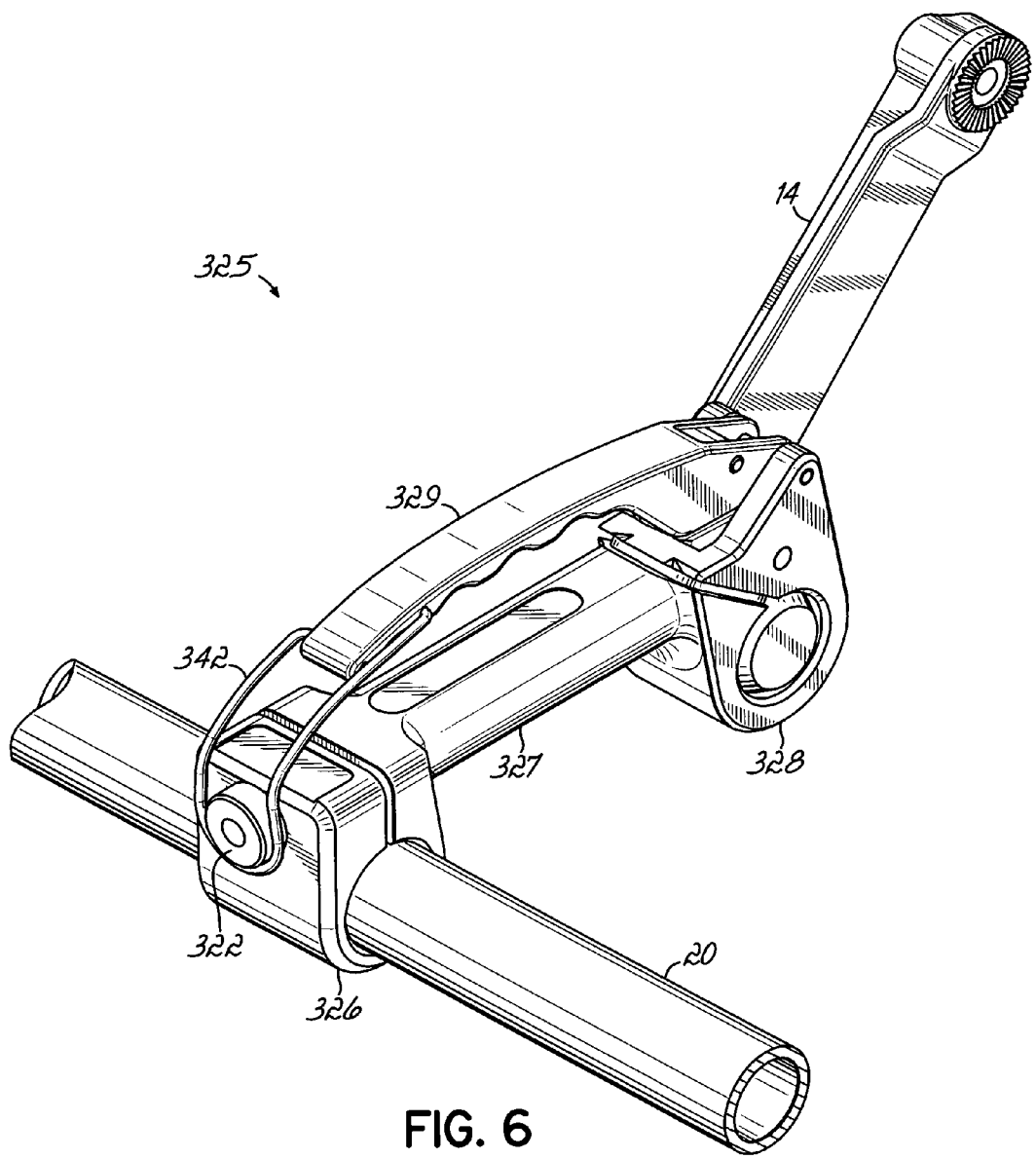
FIG. 6 is a perspective view of another variation of the invention, namely a wire catch for affirmatively securing the lever in the locked position.

The present invention also contemplates that the locking feature could be adapted to existing conventional based units. More specifically, FIG. 6 shows a conventional handle assembly 325 with spaced first and second clamps 326 and 328, an elongated body 327, and a lever 329 which has been modified to be secured in the locked position. More specifically, a wire catch 342 is mounted to a free end of the lever 329. The wire catch 342 secures to an existing bolt 322 located adjacent the first clamp 326. The wire catch 342 is rotatable relative to the lever 329, to enable affirmative locking of the lever 329, or affirmative unlocking of the lever 329.

While the present application discloses and describes a particular structure for achieving axial rotatability of first and second sections of a handle assembly in a head support system, those skilled in the art will appreciate that the disclosed material represents the presently preferred embodiments of this invention. Those skilled in the art will readily appreciate that the various aspects and embodiments shown in the present application are susceptible to reasonable structural modification, without departing from the invention. Applicants understand that the claims appended hereto will be read and interpreted in light of this specification, but applicants do not intend for the specific structural details of the specification to be read into these claims. Thus, applicants intend that the following claims should be interpreted as broadly as reasonable possible, to encompass the full scope of this invention.

We claim:

1. An apparatus for mounting a patient head support device relative to a medical table comprising:

a base unit mountable to the table, the base unit including a connecting tube oriented along a first axis, and a first handle assembly having a first end operatively connected to the connecting tube and also having a second end;

the first handle assembly further including an elongated body oriented along a handle axis and a lever hingedly connected to the elongated body, the lever hingedly movable between a locked position and an unlocked position, wherein in the locked position the first handle assembly is fixed in position at the first axis relative to the connecting tube, and in the unlocked position the first handle assembly is: a) rotatable about the first axis; and b) also rotatable about the handle axis, the elongated body further comprising:

a first section at the first end and a second section at the second end, the second section being rotatable about the handle axis relative to the first section when the lever is in the unlocked position; and a clutch mechanism carried within the first and second ends, the clutch mechanism being operable to engageably lock together the first and second sections when the first hand assembly is in the locked position.

2. The apparatus of claim 1 wherein in the unlocked position the first handle assembly is also movable along the first axis and the connecting tube.

3. The apparatus of claim 1, further comprising:
a link having opposite ends, one of the ends connected to the second end of the first handle assembly;
a like second handle assembly, similar to the first handle assembly, connected to another of the ends of the link, the second handle assembly also having respective first and second additional spaced bores, and the additional second bore being axially rotatable about the second handle axis relative to the additional first bore, the first and second handle assemblies enabling enhanced maneuverability in positioning and then locking the patient head holding device in a desired position relative to the table.

4. The apparatus of claim 1, the clutch mechanism further comprising:
first and second axially aligned ratchets held by the first and second sections, respectively; and
an axial spring carried by the handle body between the first and second sections, the spring biased to hold the first and second ratchets in an axially spaced position when the lever is in the unlocked position, thereby to allow rotation of the second section relative to the first section, the spring being axially compressible upon movement of the lever to the locked position, thereby to cause the opposing first and second ratchets to axially engage so as to prevent rotation of the second section relative to the first section.

5. The apparatus of claim 4 wherein the handle assembly further comprises:
an extension bar extending along the body and secured to the first and second ends thereof, the extension bar operatively connected to the lever such that when the lever is in the locked position, the extension bar supplies axially directed force to pull the first and second ends together and thereby reduce the internal dimensions of first and second bores located at the respective first and second ends of the body, the bar extending axially through the first and second ratchets and the spring.

6. A head support system comprising:
a medical table;
a base unit mounted to the patient table, the base unit including:
a crossbar;
a first handle assembly, the first handle assembly having an elongated body with first and second bores located at first and second ends thereof, the first and second bores defining first and second axes therethrough, respectively, the first bore encircling the crossbar, the elongated body defining a handle axis;
a lever hingedly connected to the elongated body and movable relative to the body between a closed position and an open position, wherein in the closed position the first handle assembly remains fixed relative to the crossbar, and in the open position the elongated body is rotatable relative to the first axis and the crossbar, and in the open position the second end of the elongated body is axially rotatable about the handle axis so that the second bore and the second axis can be oriented at a desired angle relative to the first axis wherein the elongated body includes;
a first section at the first end and a second section at the second end, the second section being rotatable about the handle axis relative to the first section when the lever is in the unlocked position; and
a clutch mechanism carried within the first and second ends, the clutch mechanism being operable to engageably lock together the first and second sections when the first handle assembly is in the locked position; and
a head holding device operatively supported by the base unit in a desired position relative to the medical table, the head holding device being rotatable about the handle axis when the lever is in the open position and fixed relative to the handle axis when the lever is in the closed position.

7. The bead support system of claim 6 wherein the head holding device is a skull clamp.

8. The head support system of claim 6 wherein the head holding device is also movable relative to both the first axis and the second axis when the lever is in the open position, and is fixed relative to the first axis and the second axis when the lever is in the closed position.

9. The head support system of claim 6 further comprising:
at least one additional like handle assembly interconnected between the medical table and the head holding device, thereby to enhance the maneuverability of the head holding device relative to the medical table and to facilitate the securement of a patient in a desired position relative to the table.

10. The head support system of claim 9 further comprising:
a link interconnected between the first handle assembly and the at least one additional handle assembly.

11. A head support system comprising:
a medical table;
a bracket mounted to the patient table, the bracket including a crossbar;
a first handle assembly, the first handle assembly having;
an elongated body with first and second bores located at first and second ends thereof, the first and second bores defining first and second axes therethrough, respectively, the first bore encircling the crossbar, the elongated body defining a handle axis;
a lever hingedly connected to the elongated body and movable relative to the elongated body between a closed position and an open position, wherein in the closed position the first handle assembly remains fixed relative to the crossbar, and in the open position the elongated body is rotatable relative to the first axis and the crossbar, and in the open position the second end of the elongated body is also axially rotatable about the handle axis so that the second bore and the second axis can be oriented at a desired angle which is non-parallel to the first axis wherein the elongated body includes;
a first section at the first end and a second section at the second end, the second section being rotatable about the handle axis relative to the first section when the lever is in the unlocked position; and
a clutch mechanism carried within the first and second ends, the clutch mechanism being operable to engageably lock together the first and second sections when the first handle assembly is in the locked position;
at least one additional like handle assembly operatively connected to the second end of the first handle assembly, the additional handle assembly including a respective additional elongated body defining an additional handle axis, and an additional lever which opens and closes to permit and prevent, respectively, axial rotation of an outermost end of the additional handle assembly relative to an innermost end thereof; and
a head holding device operatively connected to the additional handle assembly in a desired position relative to the medical table, the head holding device being rotatable about the first handle axis when the lever is in the open position and fixed relative to the first handle axis when the lever is in the closed position, the head holding device also being rotatable about the additional handle axis when the additional lever is in the open position and fixed relative to the additional handle axis when the additional lever is in the closed position, thereby to enhance the maneuverability of the head holding device relative to the medical table and to facilitate the securement of a patient in a desired position relative to the table.

12. The head support system of claim 11 wherein the head holding device is a skull clamp.

13. The head support system of claim 11 further comprising:
   a link interconnected between the first handle assembly and the one additional like handle assembly; and
   a transitional member interconnected between the at least one additional handle assembly and the head holding device.

14. The head support system of claim 11 and further comprising:
   an internal clutch mechanism located within the first handle assembly and operatively connected to the lever to control the axial rotatability about the handle axis; and
   an additional like internal clutch mechanism located within the additional handle assembly, and operatively connected to the additional lever to control axial rotatability about the additional handle axis.

15. An apparatus for mounting a patient head support device relative to a medical table comprising:
   a base unit mountable to the table, the base unit including a connecting tube oriented along a first axis, and a first handle assembly having a first end operatively connected to the connecting tube and also having a second end;
   the first handle assembly further including an elongated body oriented along a handle axis and a lever hingedly connected to the elongated body, the lever hingedly movable between a locked position and an unlocked position, wherein in the locked position the first handle assembly is fixed in position at the first axis relative to the connecting tube, and in the unlocked position the first handle assembly is rotatable about the first axis; and
   a latch pivotally mounted on the lever, the latch including a catch to engage the lever to releasably hold the lever in the locked position until the latch is selectively pivoted relative to the lever.

16. An apparatus for mounting a patient head support device relative to a medical table further comprising:
   a base unit mountable to the table, the base unit including a connecting tube oriented along a first axis, and a first handle assembly having a first end operatively connected to the connecting tube and also having a second end;
   the first handle assembly further including an elongated body oriented along a handle axis and a lever hingedly connected to the elongated body, the lever hingedly movable between a locked position and an unlocked position, wherein in the locked position the first handle assembly is fixed in position at the first axis relative to the connecting tube, and in the unlocked position the first handle assembly is rotatable about the first axis; and
   a wire catch mounted to a free end of the lever and operable to selectively engage the first end of the handle assembly, thereby to releasably retain the lever in the locked position.

* * * * *